United States Patent [19]
McSpadden

[11] Patent Number: 5,938,440
[45] Date of Patent: Aug. 17, 1999

[54] ENDODONTIC INSTRUMENT

[75] Inventor: John T. McSpadden, Chattanooga, Tenn.

[73] Assignee: Ormco Corporation, Orange, Calif.

[21] Appl. No.: 08/844,142

[22] Filed: Apr. 18, 1997

Related U.S. Application Data

[62] Division of application No. 08/570,283, Dec. 11, 1995.

[51] Int. Cl.⁶ ........................................ A61C 5/02
[52] U.S. Cl. .............................. 433/102; 433/224
[58] Field of Search ................... 433/102, 81, 224

[56] References Cited

U.S. PATENT DOCUMENTS

| | | | |
|---|---|---|---|
| 443,297 | 12/1890 | Sellers | 408/213 |
| 453,254 | 6/1891 | Bryant | 433/165 |
| 1,022,838 | 4/1912 | Funk | 433/102 |
| 1,067,015 | 7/1913 | Fowler | 433/102 |
| 1,211,537 | 1/1917 | Burton | 175/392 |
| 1,307,446 | 6/1919 | Kerr | 433/102 |
| 2,035,298 | 3/1936 | Caldwell | 408/230 |
| 2,084,737 | 6/1937 | Magnus | 408/230 |
| 2,328,629 | 9/1943 | Eich et al. | 408/230 |
| 2,769,355 | 11/1956 | Crisp | 408/230 |
| 2,966,081 | 12/1960 | Kallio | 408/230 |
| 3,387,511 | 6/1968 | Ackart, Sr. et al. | 408/230 |
| 3,443,459 | 5/1969 | Mackey et al. | 408/230 |
| 3,947,143 | 3/1976 | Gulla | 408/230 |
| 3,971,135 | 7/1976 | Leu | 433/165 |
| 3,991,454 | 11/1976 | Wale | 408/210 |
| 4,190,386 | 2/1980 | Brabetz et al. | 408/230 |
| 4,209,275 | 6/1980 | Kim | 408/211 |
| 4,330,229 | 5/1982 | Croydon | 408/212 |
| 4,332,561 | 6/1982 | McSpadden | 433/102 |
| 4,457,710 | 7/1984 | McSpadden | 433/81 |
| 4,536,159 | 8/1985 | Roane | 433/102 |
| 4,538,989 | 9/1985 | Apairo et al. | 433/102 |
| 4,602,900 | 7/1986 | Apairo et al. | 408/230 |
| 4,661,061 | 4/1987 | Martin | 433/102 |
| 4,758,156 | 7/1988 | Johnson | 433/81 |
| 4,894,011 | 1/1990 | Johnson | 433/81 |
| 4,904,185 | 2/1990 | McSpadden | 433/102 |
| 4,913,603 | 4/1990 | Friedli et al. | 408/230 |
| 4,934,934 | 6/1990 | Arpaio et al. | 433/102 |

(List continued on next page.)

FOREIGN PATENT DOCUMENTS

| | | |
|---|---|---|
| 0019536 | 11/1980 | European Pat. Off. . |
| 0195838 | 12/1989 | European Pat. Off. . |
| 775073 | 12/1934 | France . |
| 2537430 | 6/1984 | France . |
| 279144 | 10/1913 | Germany . |
| 949002 | 3/1956 | Germany . |
| 3429277 | 2/1986 | Germany . |
| 623224A5 | 5/1981 | Switzerland . |
| 622588 | 9/1978 | U.S.S.R. . |
| 715238 | 2/1980 | U.S.S.R. . |
| 1419624 | 12/1975 | United Kingdom . |
| 2035806 | 6/1980 | United Kingdom . |
| 2059778 | 4/1981 | United Kingdom . |

OTHER PUBLICATIONS

Metal Cutting Tool Handbook Published by Metal Cutting Tool Institute (Jul. 1965).

Der Wirkungsmechanismus der Wurzelkanal–Erweiterer, J. Walter, Budapest (including English translation: The Effective Mechanism of Root Canal Reamers, J. Walter, Budapest).

*Primary Examiner*—John J. Wilson
*Attorney, Agent, or Firm*—Wood, Herron & Evans, L.L.P.

[57] ABSTRACT

The present invention disclosed herein is directed to improved endodontic dental instruments for extirpating and/or obturating a root canal. The dental instruments of the invention have at least one friction reducing element which assists in the removal of material from a tooth canal and which reduces frictional loads on the instrument during extirpating and obturating procedures.

16 Claims, 14 Drawing Sheets

U.S. PATENT DOCUMENTS

| | | | |
|---|---|---|---|
| 5,035,617 | 7/1991 | McSpadden | 433/102 |
| 5,035,618 | 7/1991 | Katz | 433/102 |
| 5,088,863 | 2/1992 | Imanaga | 408/230 |
| 5,104,316 | 4/1992 | McSpadden | 433/102 |
| 5,106,298 | 4/1992 | Heath et al. | 433/102 |
| 5,219,284 | 6/1993 | Velvarte | 433/102 |
| 5,230,593 | 7/1993 | Imanaga | 408/230 |
| 5,236,357 | 8/1993 | Randin | 433/102 |
| 5,380,200 | 1/1995 | Heath et al. | 433/102 |
| 5,387,059 | 2/1995 | Borzemsky | 433/165 |
| 5,429,504 | 7/1995 | Peltier et al. | 433/165 |
| 5,464,362 | 11/1995 | Heath et al. | 433/102 |
| 5,735,689 | 4/1998 | McSpadden | 433/102 |

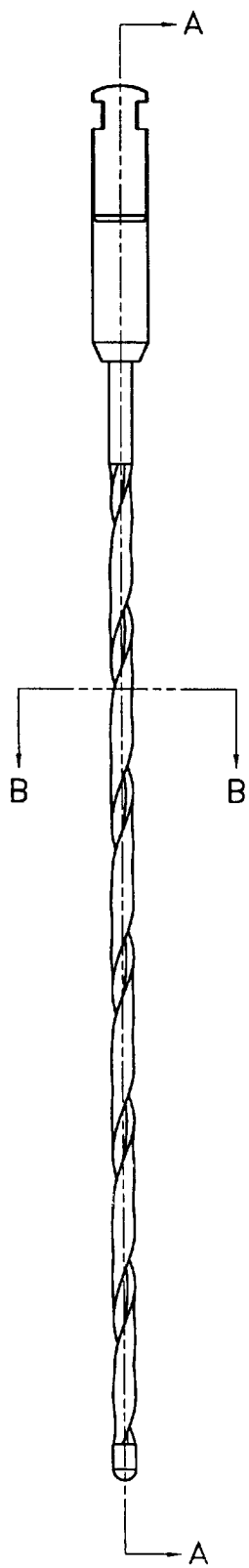
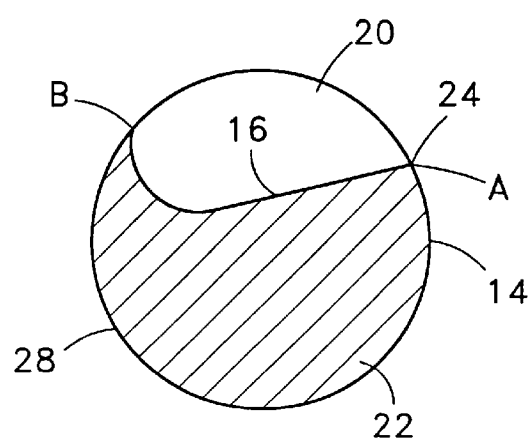
B-B
FIG.2
A-A
FIG.3
FIG.1

B-B

A-A

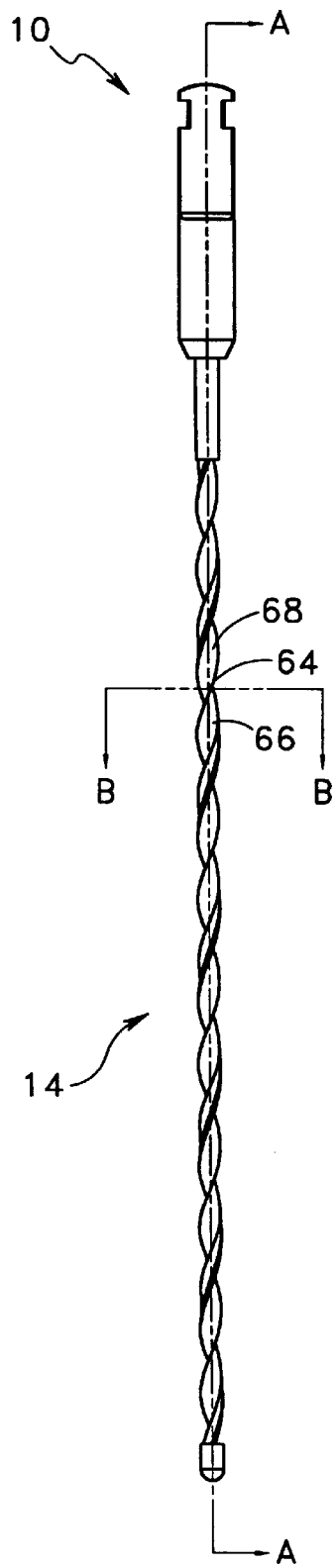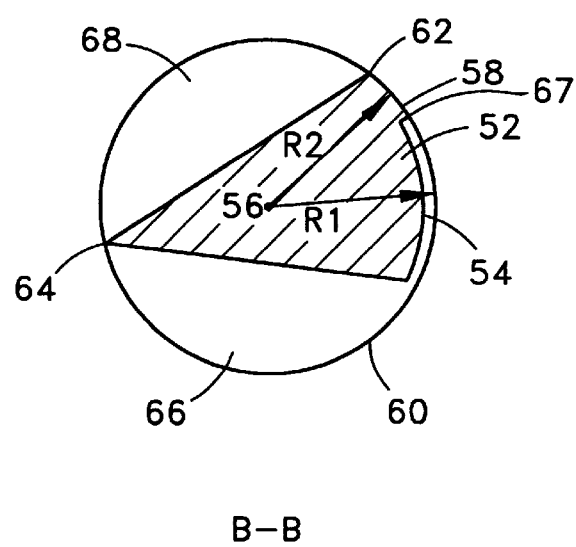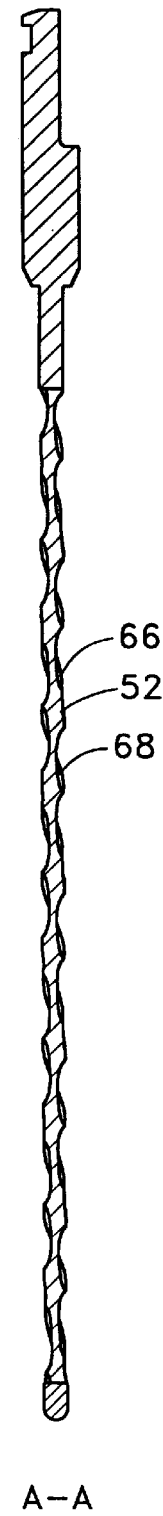
FIG.5A
FIG.5B
FIG.5C

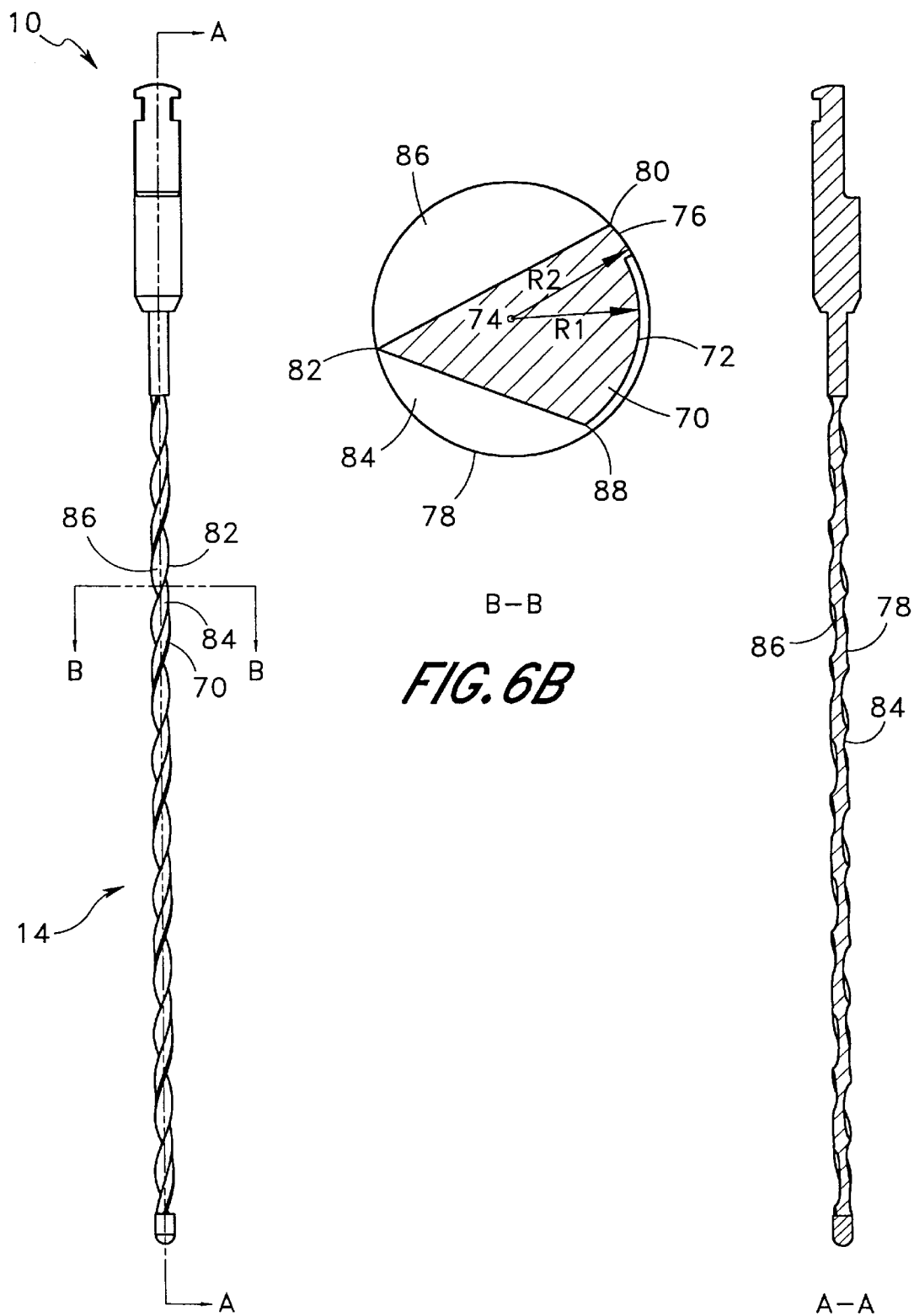

B-B

A-A

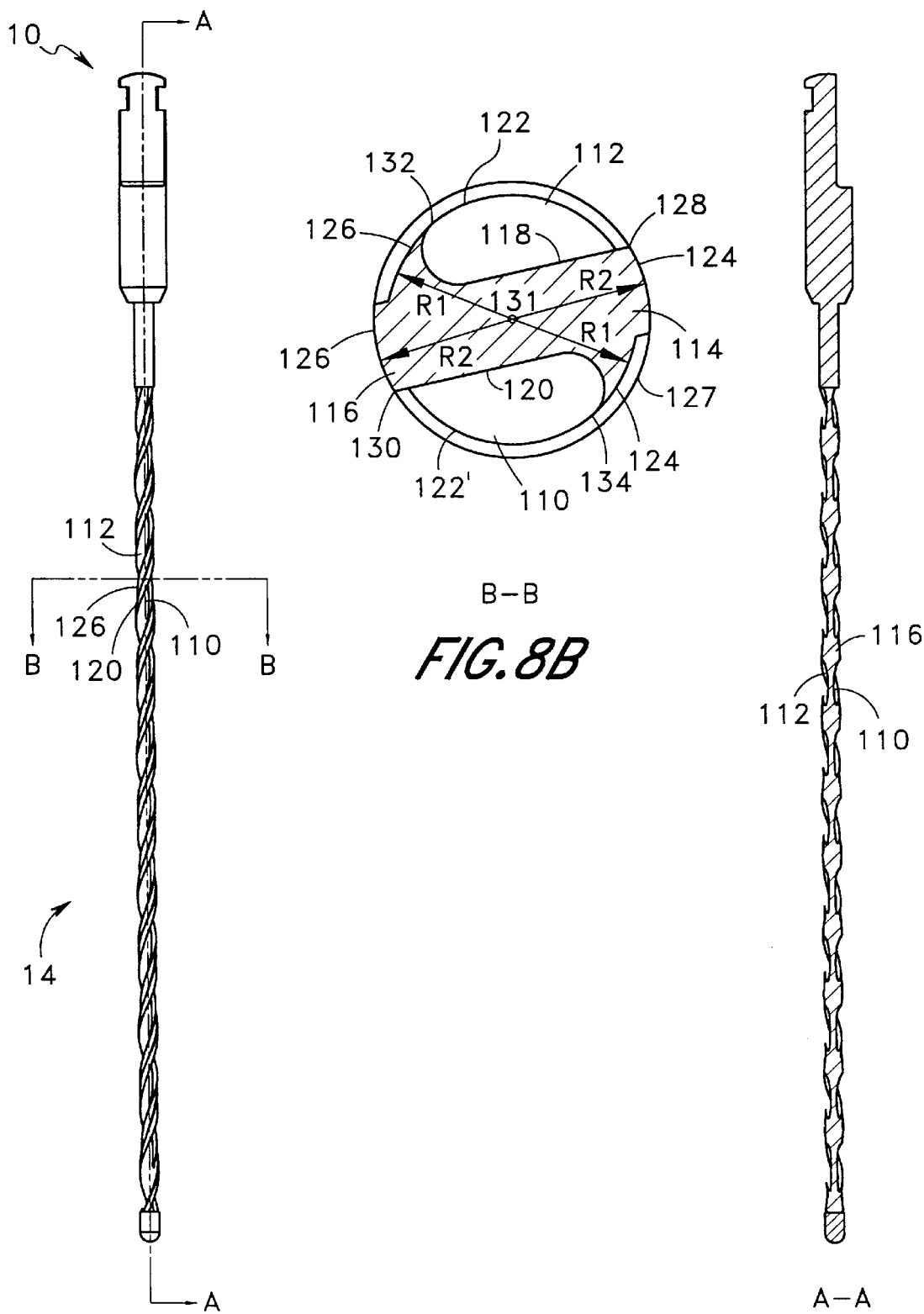

B-B

A-A

B-B

A-A

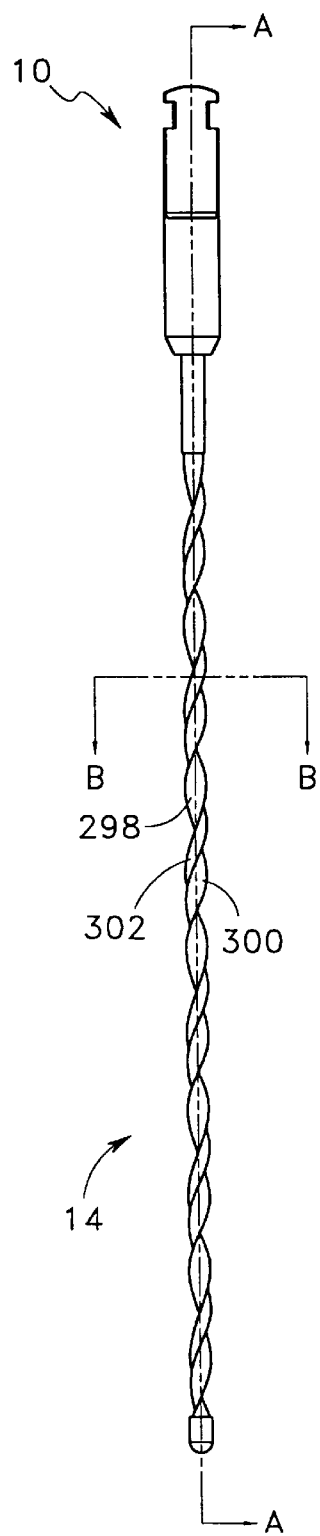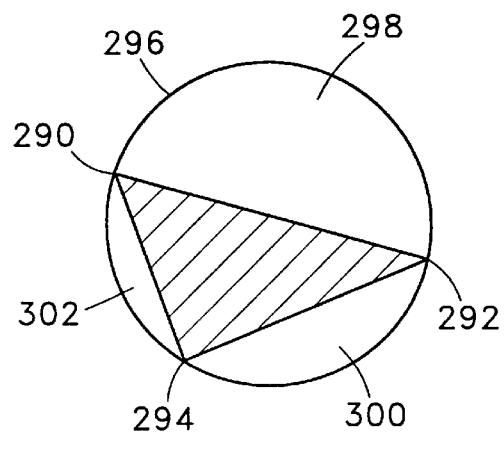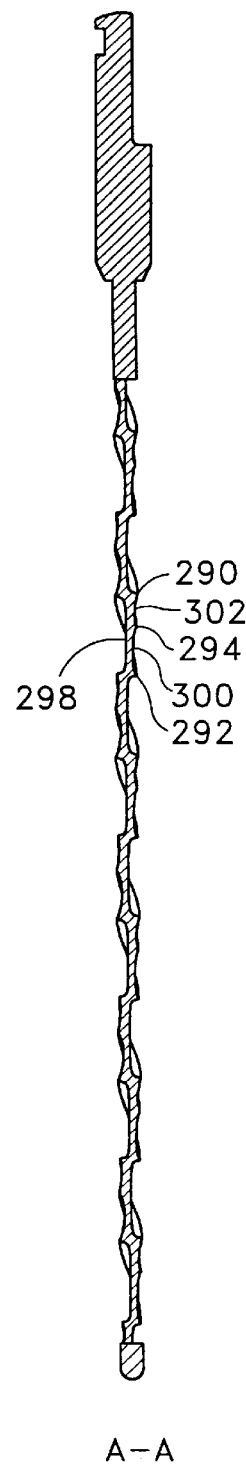
B-B
FIG.14B
FIG.14A
A-A
FIG.14C

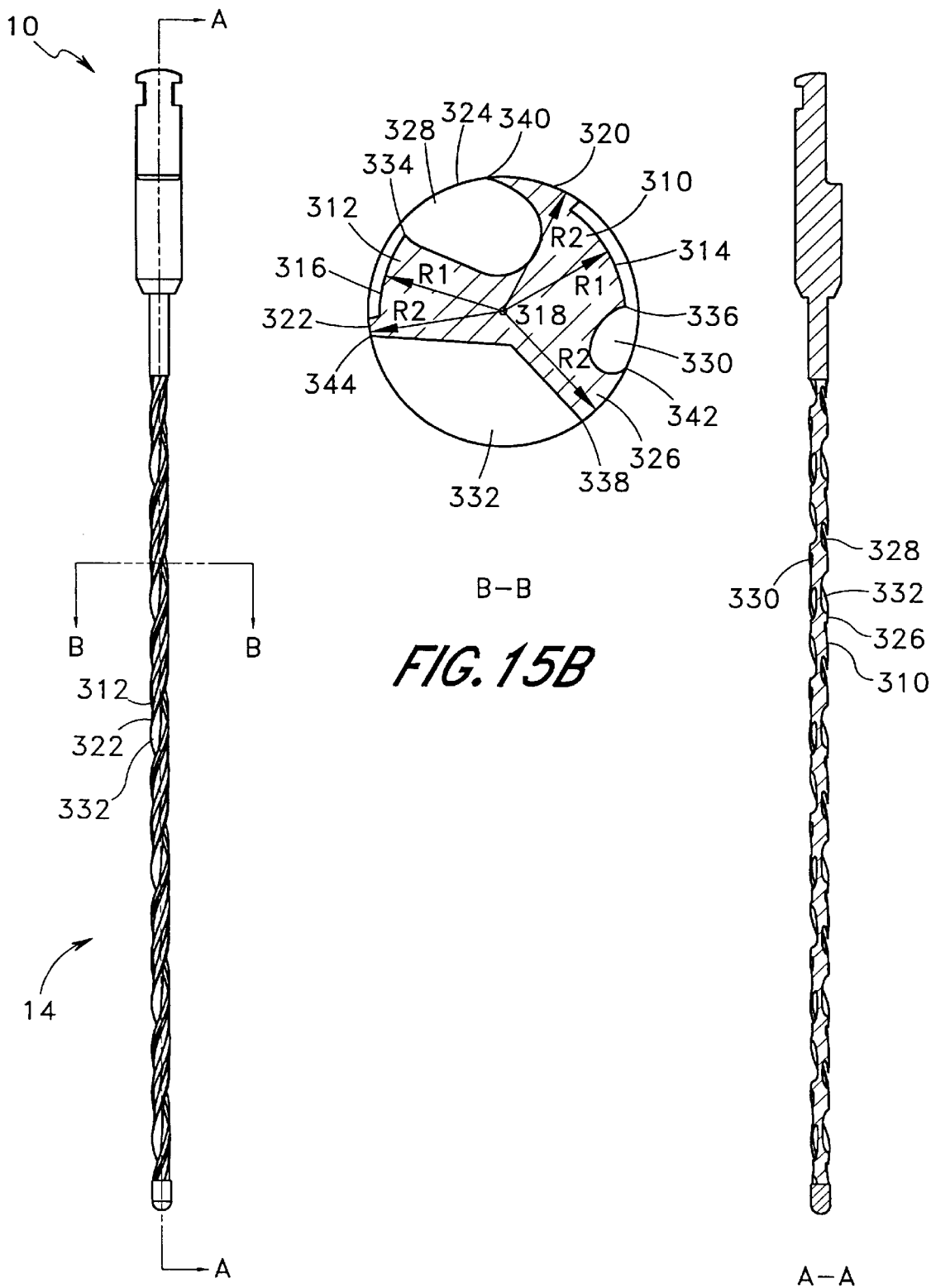

B-B

A-A

ENDODONTIC INSTRUMENT

This application is a Divisional of Ser. No. 08/570,283, filed Dec. 11, 1995.

FIELD OF INVENTION

The invention relates generally to the field of endodontics and more particularly to reamers and condensers used in performing root canal procedures. The reamers are used to remove diseased tissue from the canal and the condenser is used to place sealing and filling material in the prepared canal cavity after removal of the diseased material.

BACKGROUND OF THE INVENTION

The circulatory and neural systems of the tooth enter the tooth at the terminus of each of its roots and extend through a narrow, tapered canal system to a pulp chamber adjacent the crown portion of the tooth. If the pulp tissue becomes diseased, extraction of the tooth can often be avoided by removing the diseased tissue and sealing the canal system in its entirety. Endodontic files and reamers are tapered instruments used to remove the diseased tissue in the root canal by reciprocating and/or rotating the instruments in the canal. Since many root canals are small, curved and calcified, the instruments must be able to withstand the torsional load necessary to enlarge the canal without breaking the instrument thus further complicating the treatment.

Once as much of the diseased material as practicable is removed from the root canal, the canal is sealed closed, typically by reciprocating and/or rotating a condenser instrument in the canal to urge a sealing material such as gutta-percha into the canal. Gutta percha used as a sealing material has a high viscosity and thermoplastic character and since the canals are usually small and curved, it is also desirable to use a condenser instrument which is able to withstand the torsional load necessary to urge the material into the canal without breaking the instrument while at the same time condensing the sealing material without leaving any voids in the canal which may lead to treatment failure.

One of the problems with traditional endodontic instruments used for extirpating and filling a root canal is that the torsional limitations of the instrument are often exceeded resulting in breakage of the instrument. Breakage of the instrument may occur as a result of the inadequate removal of dental chips which are cut from the wall of the root canal. The dental chips may be engaged between the instrument and the root canal wall resulting in friction which may cause excessive torque and thus breakage of the instrument.

Traditional reamers or files contain helical flutes along the working portion which are substantially semi-circular in cross-section, that is, an arc tracing a line transverse to the flute length along the bottom of the flute wall is of substantially uniform radii at all points along the line. This structure is intended to promote advancement of tooth chips and debris up the expanding diameter of the instrument along the spiraling flute away from the tip. However, during the extirpating procedure, the dental chips which are formed may be inadequately removed from the root canal and may be forced into flutes along the instrument between the instrument and the root canal causing damage to the canal walls and/or inadequate or uneven tissue removal. This build up of debris may also lead to increased friction resistance already imposed by contact between the instrument and the canal, which in turn increases the torsional load on the instrument. In many cases, the torsional loads on the instrument exceed the tensile strength of the working portion of the instrument resulting in fracture.

It is therefore an object of the invention to provide an endodontic dental instrument which reduces the friction load on the instrument in the root canal.

It is another object of the invention to provide an endodontic dental instrument having a reduced tendency to break during use.

Still another object of the invention is to provide a condenser instrument which more effectively, introduces and condenses a sealing material into an extirpated root canal.

Yet another feature of the invention is to provide a reamer which more effectively removes damaged or diseased tissue from a root canal, thus decreasing friction during root canal cleaning and extirpation and improving the uniformity of the tissue removal from all affected portions of the canal and its defining wall.

SUMMARY OF THE INVENTION

With regard to the foregoing and other objects, the present invention is directed to an improved endodontic instrument which comprises an elongate working portion, which may be tapered or of substantially uniform cross-sectional diameter, extending between adjacent a base or proximate end and adjacent a tip or distal end. The working portion has a length of from about 3 to about 18 millimeters and a peripheral diameter ranging from about 0.08 millimeters to about 1.9 millimeters, and includes at least one helical flute, at least one helical land adjacent the flute in working cooperation therewith with a tissue removing edge therebetween and a point distal from the tissue removing edge, each flute and land having a pitch ranging from about 1 spiral per 16 millimeters to about 1 spiral per millimeter for use in an endodontic procedure. The working portion is adapted through provision of one or more friction reducing elements to reduce friction between the instrument and the canal to improve the performance of the instrument while reducing the tendency of the instrument to fail under torsional stresses.

In one friction reducing embodiment, the point distal from the tissue removing edge adjacent the periphery, in cross-section, recedes from the periphery at from about an acute angle with respect to a line tangent to the periphery at the point of intersection. The angle is measured from the side of the tangent line distal from the tissue removing edge.

In another embodiment, the endodontic instrument has at least one outer land, when viewed in cross-section, adjacent the periphery defined by the tissue removing edge and at least one recessed land. The outer land and the recessed land may be adjacent one another or separated by at least two flutes.

In yet another embodiment, the endodontic instrument comprises at least two flutes spaced apart by a tissue removing edge or a land which flutes have substantially unequal dimensions when viewed in cross-section. The flutes are parallel along the working length meaning that they extend along helical paths that do not intersect each other. An endodontic instrument of the invention may also comprise a combination of two or more of the foregoing friction reducing elements.

BRIEF DESCRIPTION OF THE DRAWINGS

The above and other features and advantages of the present invention will now be further described in the following detailed description in conjunction with the accompanying drawings in which:

FIG. 1 is an elevational view of a reamer instrument according to one embodiment of the invention;

FIG. 2 is a cross-section view of the reamer instrument of FIG. 1 taken along line B—B thereof;

FIG. 3 is a longitudinal view in section of the reamer instrument of FIG. 1 taken along line A—A thereof;

DETAILED DESCRIPTION OF THE PREFERRED EMBODIMENTS

Figure 4A:
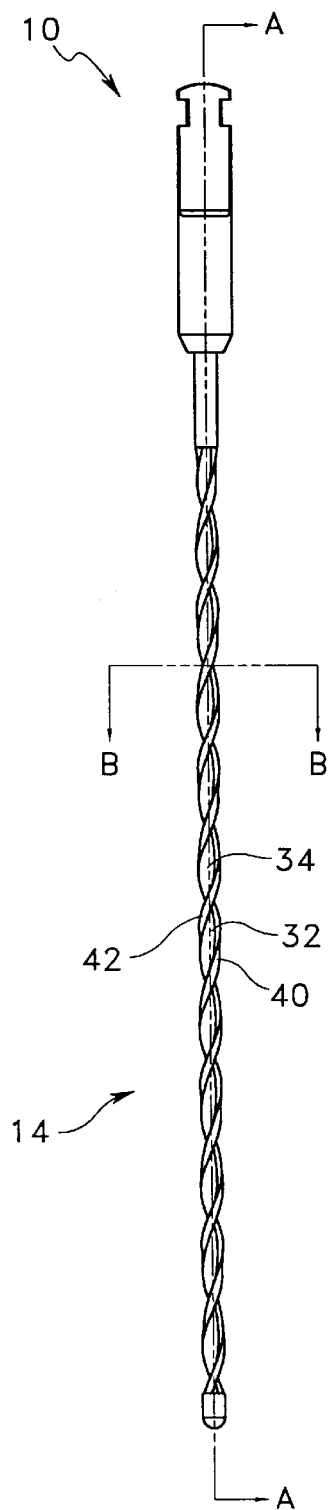
FIGS. 4A–C through 16A–C are elevational, longitudinal and cross-sectional views of various designs of endodontic instruments according to the invention.

FIGS. 1–16 illustrate endodontic instruments having various working portion configurations within the scope of the invention. The instruments may be used as reamers or condensers depending on the direction of twist of the helical flutes and lands with respect to the direction of rotation of the instrument.

In all of the embodiments of the invention illustrated herein, the instruments are represented as reamers. However, it will be appreciated that a mirror image of the instrument design may be used as a condenser for the same direction of rotation of the instrument. Condenser instruments made in accordance with the invention are used to fill void spaces in the root canal cavity. In all of the embodiments having multiple flutes, and as shown in the drawings, the flutes are parallel, i.e., they extend along helical paths that do not intersect each other along the working length.

With reference now to FIG. 1, there is illustrated an endodontic instrument according to one embodiment of the invention which may be used as a reamer and which has a shaft 10 having a base or proximate end 12 and an elongate working portion 14 extending between the base or proximate end 12 terminating in a tip or distal end 16. The proximate end 12 also contains a fitting portion 18 for mating with a chuck of a dental handpiece (not shown). Alternatively, or in addition to the fitting 18, the proximate end 12 may include a knurled or otherwise treated surface to facilitate hand manipulation of the reamer 10. The working portion 14 of the instrument has a length which may range from about 3 millimeters to about 18 millimeters. A preferred length is about 16 millimeters.

The working portion may have the same cross-sectional diameter between the proximate end 12 and the distal end 16 or the working portion may be tapered in either direction from the proximate end 12 to the distal end 16. When tapered, the taper of the cross-sectional diameter of the working portion 14 may range from about −0.01 to about 0.8 millimeters per millimeter, preferably from about 0.02 to about 0.06 millimeters per millimeter.

The working portion 14 is comprised of one or more helical flutes 20 and one or more helical lands 22 (one each in the embodiment of FIG. 1). In the illustrated embodiment, helical flute 20 and helical land 22 are adjacent tissue removing edge 24. Helical land 22 and tissue removing edge 24 are at the periphery of the working portion 14 while flute 20 has a surface 26 (FIGS. 2 and 3) which is recessed from the periphery of the working portion 14 which surface, in cross-section, recedes from the periphery 28 at from about an acute angle 27 with respect to a line 29 tangent to the periphery at the point of intersection B which angle is measured from the side of the tangent line 29 distal from the removing edge 24.

As shown in FIGS. 2 and 3, tissue removing edge 24 is generally opposite a portion of the helical land 22. The wall of flute 20 intersects the periphery of the working portion in the region denoted by the letter A immediately adjacent the periphery 28 of the working portion at an angle of about 90 degrees to tangent to form what is commonly referred to as a zero or neutral rake angle from the perspective of the surface 26 of the flute 20. For purposes of this invention, the rake angle of the tissue removing edge 24 may be neutral, positive or negative but is preferably about neutral.

It will be appreciated that helical land 22 presents a bearing surface between tissue removing edge 24 at point A and point B distal from the tissue removing edge (FIG. 2) so that when rotated in a canal, only edge 24 removes tissue while the bearing surface of the helical land 22 bears against the canal wall. In FIG. 2, both point A and point B are located at the periphery 28 of the working portion 14 on generally opposing sides of the land 22.

As illustrated by FIGS. 2 and 3, flute 20 has a concave surface 26 which is recessed from the periphery of the working portion, so that at point B, the surface 26 forms about an acute angle 27 with the line 29 tangent to the periphery. By providing a flute having about an acute angle at B, tissue and debris from the root canal may be more effectively transported and removed from the canal in a direction opposite to the direction of travel of the instrument as the instrument is rotated in the root canal. By removing the debris more effectively from the root canal, there is less friction on the working portion and thus less tendency to shear the instrument by the torque applied to the instrument.

For the most effective cutting and tissue removal it is preferred that the pitch of the helical flutes 20 and helical lands 22 range between about 1 spiral per 16 millimeters to about 1 spiral per millimeter along the working portion 14 of the instrument.

Figure 4B:
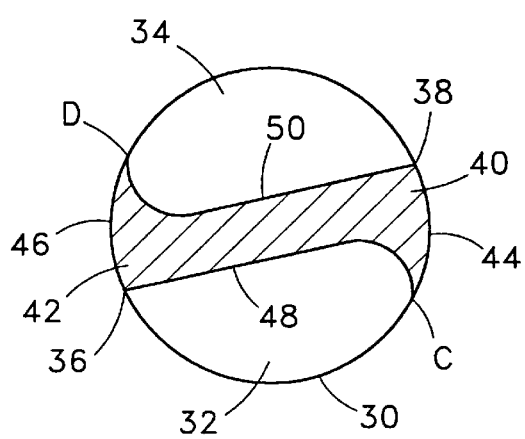
Figure 4C:
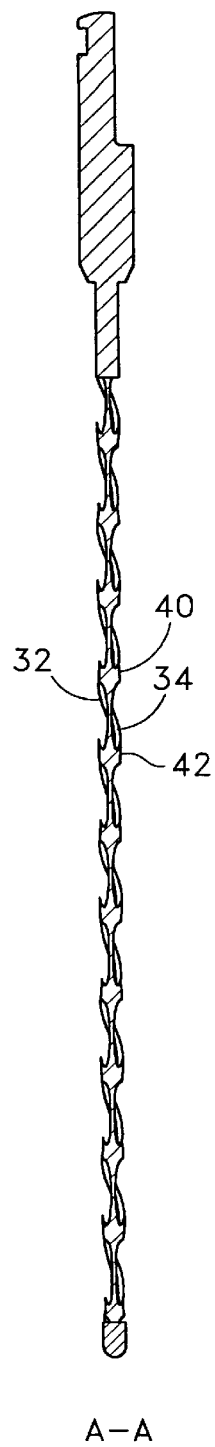

Another endodontic instrument 10 according to the first embodiment of the invention is illustrated in FIGS. 4A–C wherein FIG. 4A is an elevational view, FIG. 4B is a cross-sectional view along line B—B of FIG. 4A and FIG. 4C is a partial longitudinal view of FIG. 4A taken along line A—A thereof. The working portion 14 of the instrument illustrated by FIGS. 4A–C contains two helical flutes 32 and 34 and has tissue removing edges 36 and 38 adjacent two helical lands 40 and 42 which have bearing surfaces 44 and 46. As with the instrument illustrated in FIGS. 1–3, points C and D distal from tissue removing edges 36 and 38, respectively, form about acute angles with lines tangent to the periphery at the points of intersection as described above with reference to FIG. 2.

The working portions of endodontic instruments according to the invention may be provided with various other friction reducing designs in lieu of or in addition to the above described designs illustrated in FIGS. 1–4C. Such designs may include flutes with receding surfaces as described above, one or more recessed land portions, three or more spaced apart helical lands wherein the spacing between adjacent helical lands in cross-section varies, three or more spaced apart helical tissue removing edges, various cutting edge designs or a combination of two or more of the foregoing collection means. Cross-sectional configurations of endodontic instruments having alternative designs are illustrated in FIGS. 5A through 16C.

In FIGS. 5A through 6C, the working portion 14 of instrument 10 contains at least one outer helical land 58 adjacent the periphery defined by tissue removing edge 64 and edge 62 distal from the tissue removing edge 64 and at least one recessed land 54. As illustrated in FIG. 5B, helical land 52 has a receding wall portion 54 extending from a shoulder 57 to the flute 66 and which is a radial distance $R_1$ from the cross-sectional center 56 of the working portion and a portion 58 which is adjacent the periphery 60 of the working portion which is at a radial distance $R_2$ from the cross-sectional center 56. The periphery 60 is defined by helical tissue removing edges 64 and land portion 58. In this embodiment, helical flutes 66 and 68 are equally spaced apart about helical land 52 and tissue removing edge 64.

In FIG. 6A–C, there is again a helical land 70 having at least one outer portion 76 and at least one recessed portion 72. The recessed portion 72 which is at a radial distance $R_1$ from the cross-sectional center 74 of the working portion and a portion 76 of land 70 is adjacent the periphery 78 of the working portion at a radial distance $R_2$ from the cross-sectional center 74. The periphery 78 is defined by helical tissue removing edge 82 and point 80 distal from tissue removing edge 82. In this embodiment, the curvilinear distance between tissue removing edge 82 and point 80 of helical land 70 is greater than the curvilinear distance between tissue removing edge 82 and point 88 of helical land 70.

In the embodiments illustrated in FIGS. 5 and 6, there is a reduction of the force of tissue removing edges 64 and 82 against the wall of the root canal in the direction perpendicular to the direction of rotation of the instrument in the canal because of the recessed portions 54 and 72 of helical lands 52 and 70. A reduction in force of the tissue removing edges 64 and 82 with respect to the canal wall provides a reduction in friction during rotation of the instrument in the root canal as the instrument bends to conform to contours of the root canal cavity. The recessed wall portions of the helical lands have a radius $R_1$ which is from about 4 to about 30 percent less than radius $R_2$.

In addition to the recessed wall portions illustrated in FIGS. 5A–C, the instrument illustrated in FIGS. 6A–C also contains tissue removing edge 82 which is a greater curvilinear distance from 80 than from point 88 on helical land 70. The unequal curvilinear distances provide unequal cutting forces along the periphery 78 of the working portion of the instrument thereby producing a side-cutting effect which more readily maintains the central axis of a curved root canal.

Figure 7A:
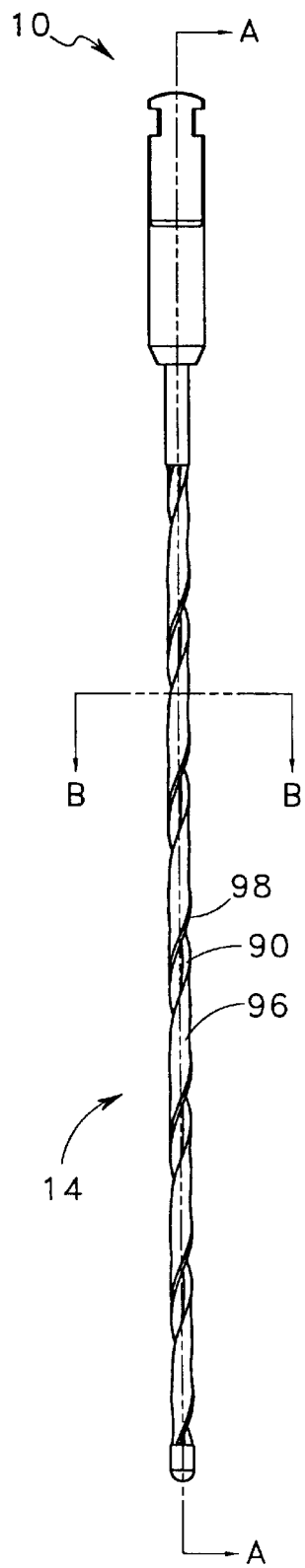

FIGS. 7A through 8C are alternative embodiments of the invention containing one or more helical flutes which have flute surfaces, in cross-section which recede from the periphery at from about an acute angle with respect to a line tangent to an inside periphery 102 at the point of intersection and one or more helical lands having recessed wall portions. The inside periphery 102 is defined by point E and recessed land portion 106. In FIGS. 7A–C, there is one helical flute 90 having a tissue removing edge 98 which intersects an outer periphery 92 of the working portion in the region immediately adjacent the outer periphery 92 of the working portion at an angle of about 90 degrees to tangent to form a zero or neutral rake angle from the perspective of the surface 94 of the flute 90.

Helical land 96 provides a bearing surface 106 between point E and tissue removing edge 98 so that when rotated in a canal, only edge 98 removes tissue while the bearing surface 106 bears against the canal wall. Helical land 96 has an outer land portion 108 adjacent the periphery 92 and a recessed land portion 106 between shoulder F and point E. Recessed land portion 106 has a cross-sectional radius $R_1$ from the cross-sectional center 104 of the working portion and outer land portion 108 has a radius of $R_2$ from the cross-sectional center 104 which is from about 4 to about 30 percent greater than radius $R_1$.

Figure 7B:
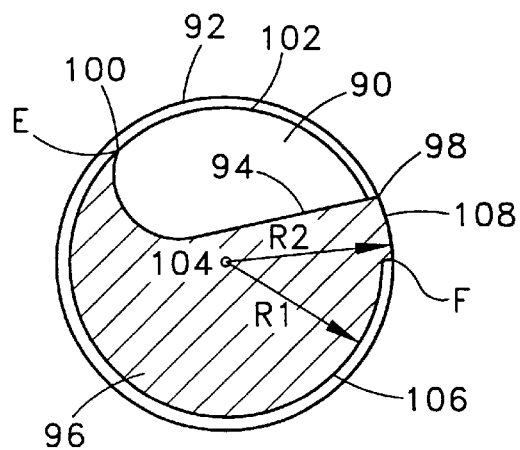
Figure 7C:
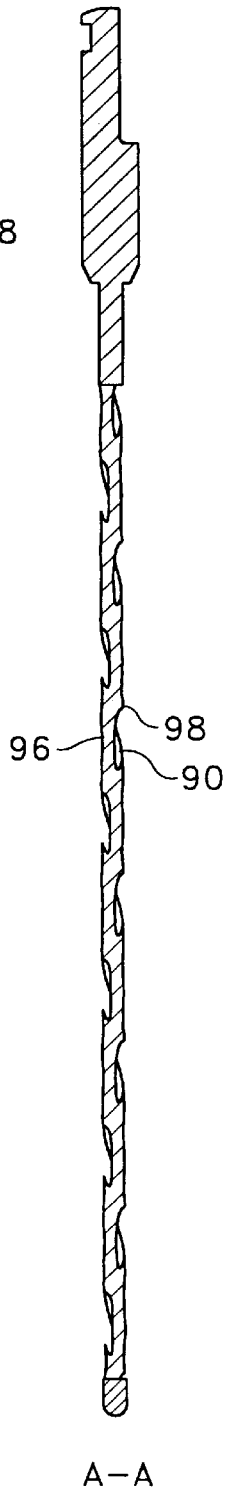

As illustrated by FIG. 7B, the surface 94 of flute 90 which, in cross-section, recedes from the inner periphery 102 at from about an acute angle with respect to a line tangent to the periphery 102 at the point of intersection as illustrate by FIG. 2 above. Flute 90 provides means for collecting and removing tissue or debris from the root canal by transporting the debris opposite to the direction of travel of the instrument as the instrument is rotated in the root canal. In combination with recessed wall portion 106 of helical land 96, the instrument 10 illustrated in FIGS. 7A–C provides reduced friction as the instrument is rotated in the canal due to uneven cutting forces and more effective tissue removal during endodontic procedures.

In FIGS. 8A–C, the endodontic instrument contains two helical flutes 110 and 112 and two helical lands 114 and 116. Helical flutes 110 and 112, as illustrated in FIG. 8B, have surfaces 118 and 120 which recede from the inner peripheries 122 and 122' with about acute angles with respect to lines tangent to the peripheries 122 and 122' at the points of intersection 132 and 134 thereof. Outer land portions 124 and 126 of helical lands 114 and 116 lie on the outer periphery 127 of the working portion of the instrument which is defined by tissue removing edges 128 and 130, while recessed wall portions 125 and 129 of helical lands 114 and 116 lie at a radial distance $R_1$ from the cross-sectional center 131 which is about 4 to about 30 percent less than radial distance $R_2$ from the center 131 to the periphery 127 of the working portion defined by tissue removing edges 128 and 130.

Figure 9A:
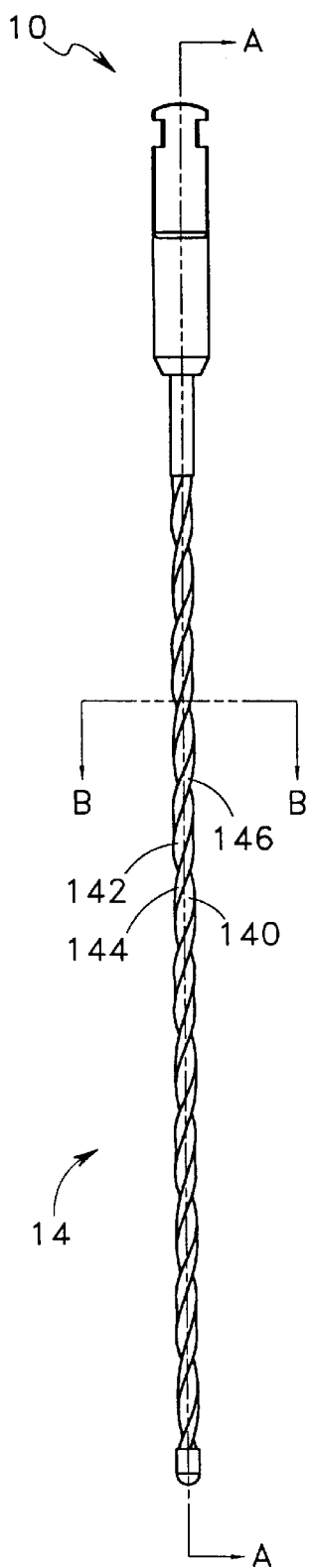
Figure 9B:
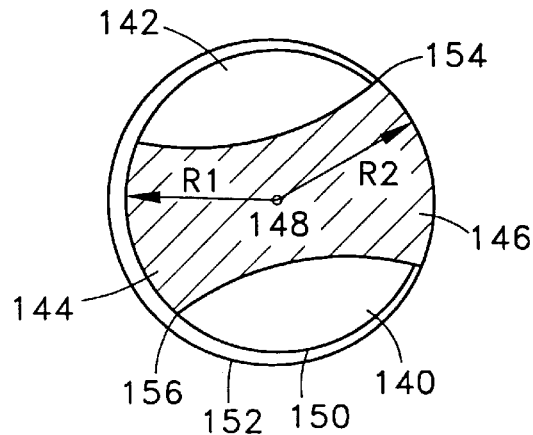
Figure 9C:
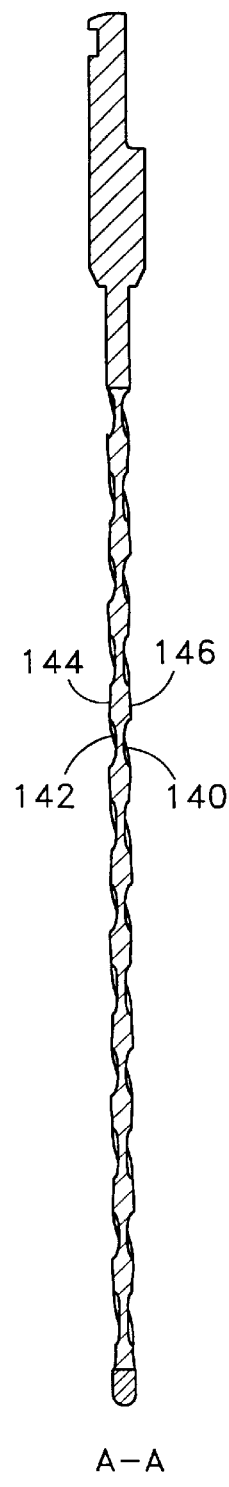

FIGS. 9A–C illustrate another instrument 10 according to the invention having a working portion 14 containing two diametrically opposed helical flutes 140 and 142 and two diametrically opposed helical lands 144 and 146. In this embodiment, land 146 is an outer land which is adjacent the outer periphery 152 defined by tissue removing edge 154 and land 144 is a recessed land which is adjacent an inner periphery 150 defined by tissue removing edge 156 as illustrated by FIG. 9B. Recessed land 144 has a radius $R_1$ from the cross-sectional center 148 to recessed land portion on inner periphery 150 and outer land 146 has a radius $R_2$ from the cross-sectional center 148 to outer periphery 152 which is 4 to 30 percent greater than distance $R_1$. An instrument of the design illustrated in FIGS. 9A–C will provide less aggressive tissue removing force with respect to the root canal wall on removing edge 154 as a result of the recessed land portion 146 than the force of removing edge 156. While helical flutes 140 and 142 are illustrated as being equally spaced with respect to removing edges 154 and 156 about the peripheries of the working portion, it will be recognized that unequal spacing of the flutes may also be used.

Figure 10A:
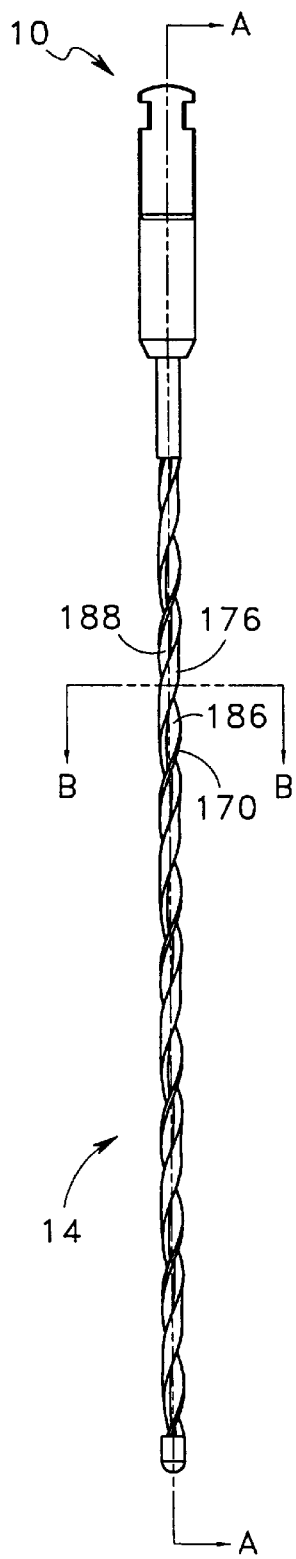
Figure 10B:
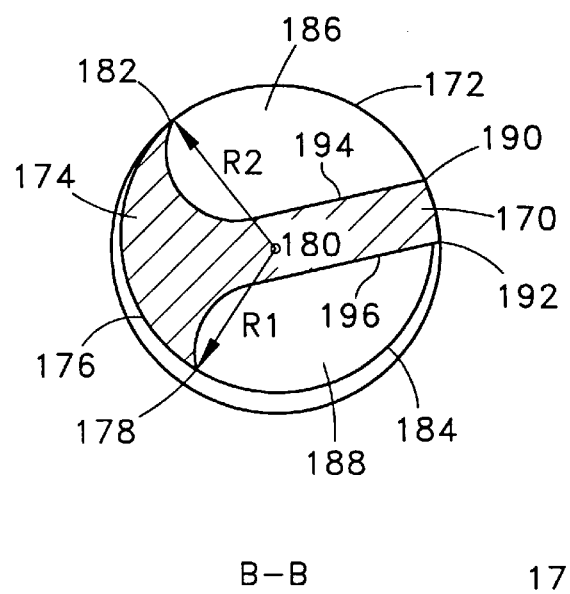
Figure 10C:
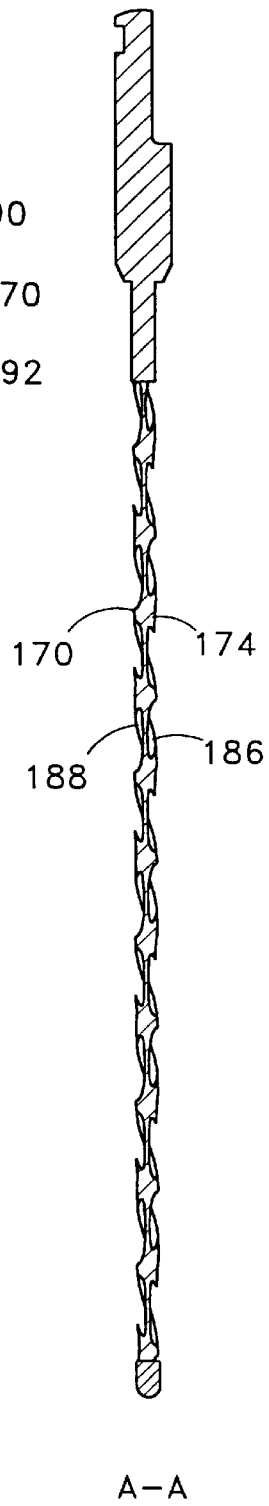

FIGS. 10A–C represent an instrument 10 according to the invention having a helical land 170 which lies on the periphery 172 of the working portion defined by tissue removing edge 190 and a helical land 174 having a recessed wall portion 176 which has a radius $R_1$ at point 178 with respect to the cross-sectional center 180 and a wall portion having a radius $R_2$ which lines on the periphery 172. The radius of the wall portion of helical land 174 gradually increases from point 178 which lies adjacent the inner periphery 184 to point 182 which lies adjacent the outer periphery 172 so that helical land 174 has an outer land portion and a recessed land portion as illustrated in FIG. 10B. The recessed portion 176 of land 174 provides a redacting in the cutting force of cutting edge 190 and therefore reduces the friction with respect to the root canal walls during rotation of the instrument.

Spaced apart helical flutes 186 and 188 of the instrument illustrated in FIGS. 10A–C each have surfaces 194 and 196, in cross section, which recede at about acute angles to lines tangent to the peripheries 172 and 184 at the points 182 and 178 respectively. FIGS. 10A–C therefore represent an endodontic instrument 10 containing a combination of a recessed land and the helical flutes described in FIGS. 1–3 which reduces friction and/or has better removal efficiency of material from the root canal during an endodontic procedure.

Figure 11A:
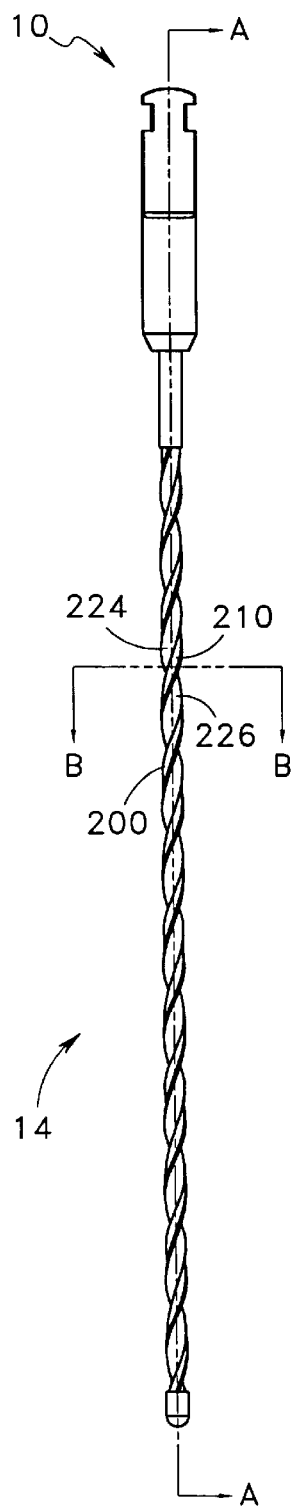
Figure 11B:
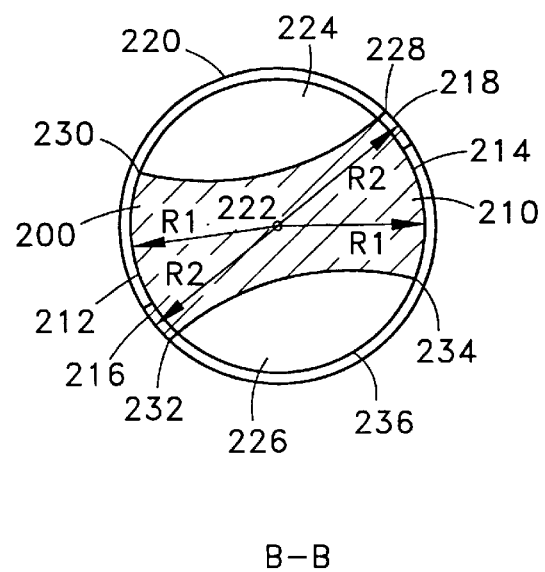
Figure 11C:
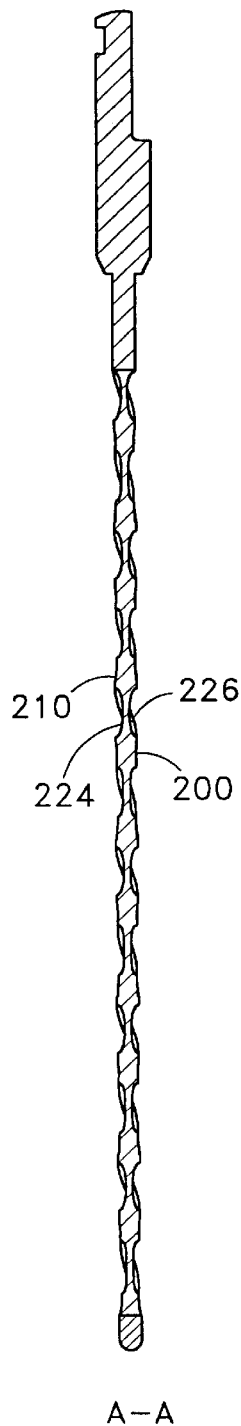

FIGS. 11 A–C provide a variation of the endodontic instrument of the invention which combines the features illustrated and described by reference to FIGS. 9A–C above with recessed land portions. In FIG. 11B, there are two opposing helical lands 200 and 210 separated by helical flutes 224 and 226. Helical land 200 has a recessed wall portion 212 and an out wall portion 216 and helical land 210 has a recessed wall portion 214 and an outer wall portion 218. The recessed wall portions 212 and 214 lie on an inner periphery 236 defined by points 230 and 234 which are distal to tissue removing edges 228 and 232. The recessed portions 212 and 214 are at a radial distance of $R_1$ in cross section from the cross-sectional center 222 of the working portion and outer land portions 216 and 218 lie at a radial distance $R_2$ from the center 222 and adjacent an outer periphery 220 of the working portion defined by tissue removing edges 228 and 232. Radius $R_2$ is at a distance which is 4 to 30 percent greater than $R_1$ with respect to the center 222. Helical flutes 224 and 226 are disposed about the periphery of the working portion so that the curvilinear distance between tissue removing edge 228 and point 230 is substantially the same as the curvilinear distance between tissue removing edge 232 and point 234. However, unequal curvilinear flute distances may also be used for increased cutting efficiency as described above with respect to FIGS. 6A–C.

Figure 12A:
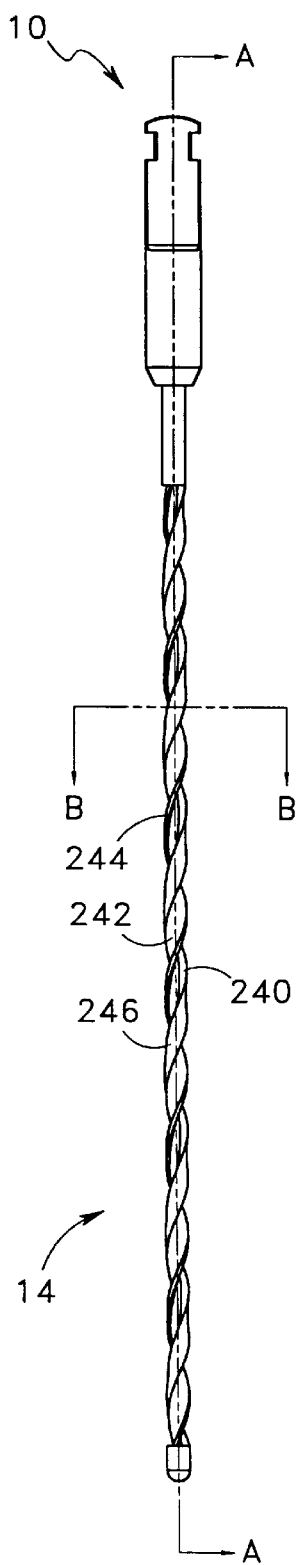
Figure 12B:
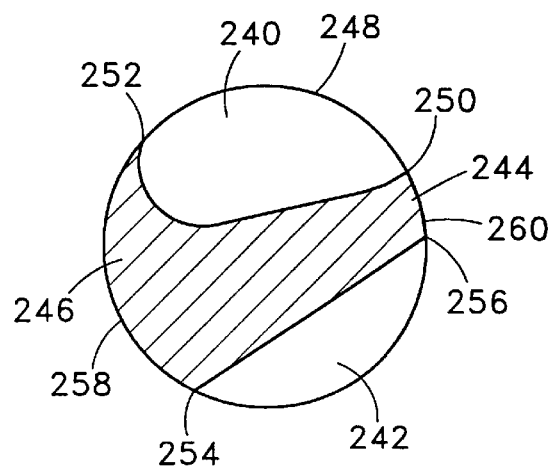
Figure 12C:
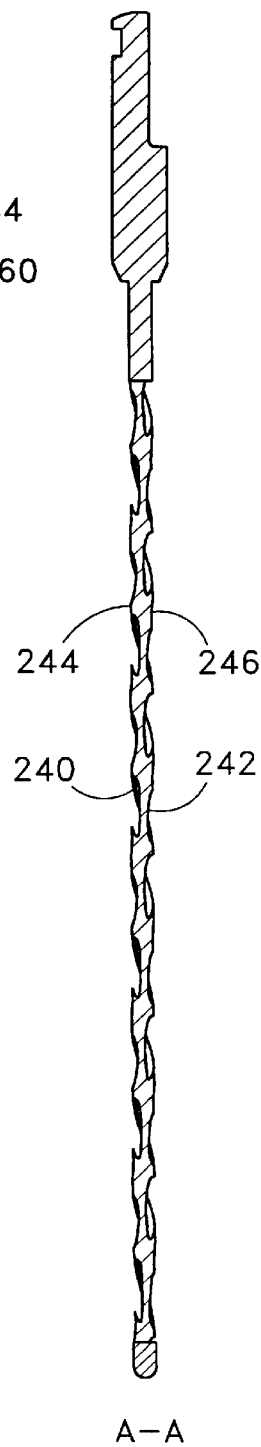

FIGS. 12A–C, illustrate a combination of the features illustrated by FIGS. 1–3 with unequally spaced flutes 240 and 242 illustrated by FIGS. 6A–C and unequally sized opposing lands 244 and 246. According to this embodiment, the working portion 14 contains at least one helical flute 240 wherein point 252 distal from tissue removing edge 250, in cross-section, recedes at about an acute angle with respect to a line tangent to the periphery 248 at the point of intersection as shown in FIG. 12B and described with reference to FIGS. 1–3 above. As illustrated by FIG. 12B, the curvilinear distance from tissue removing edge 254 to point 252 is greater than the curvilinear distance from tissue removing edge 250 to point 256. Hence the bearing surface 258 of helical land 246 is substantially greater than the bearing surface 260 of helical land 244. The unequal bearing surfaces of the lands provide unequal tissue removal efficiencies along the periphery 248 of the working portion of the instrument thereby producing a side-cutting effect which more readily maintains the central axis of a curved root canal.

Figure 13A:
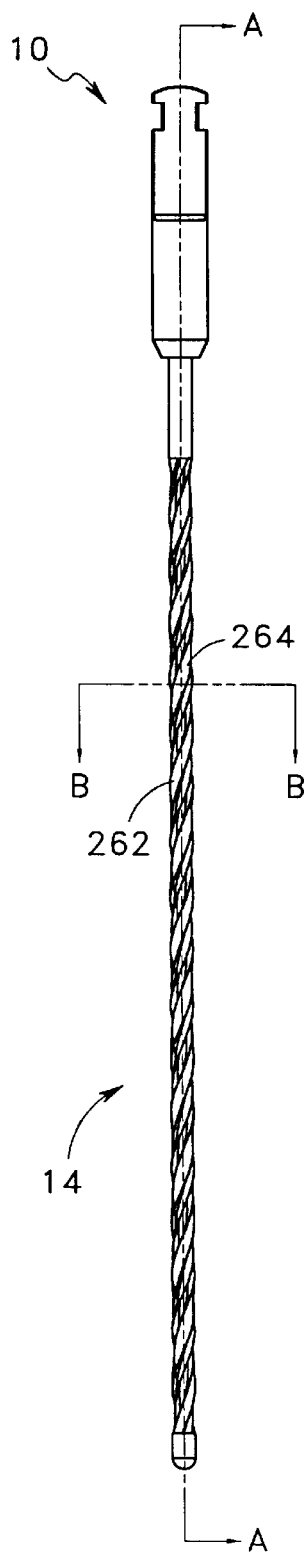
Figure 13B:
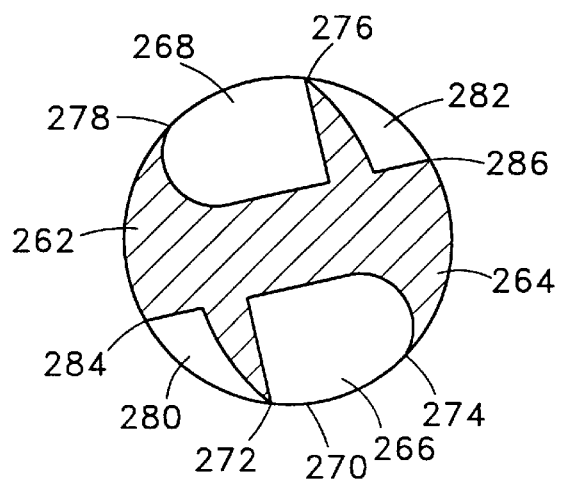
Figure 13C:
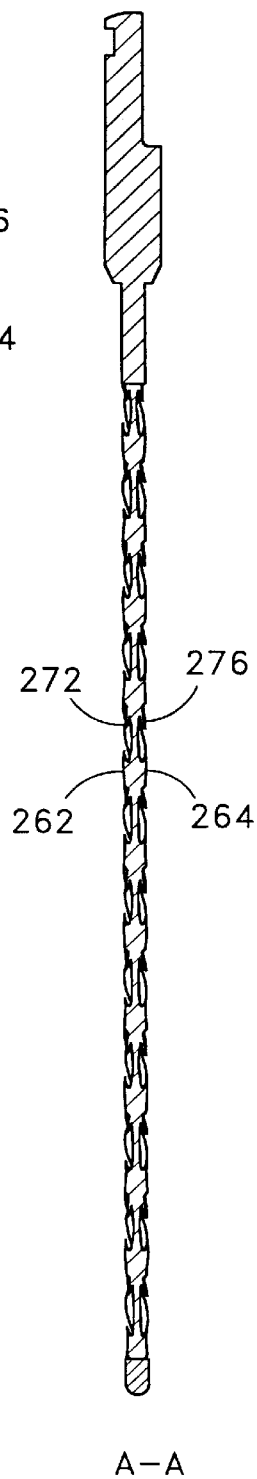

A combination of two of the before mentioned embodiments of the invention is illustrated in FIG. 13A–C. With reference to FIGS. 13B, the endodontic instrument 10 contains two helical lands 262 and 264 and two helical flutes 266 and 268. Helical flute 266 is between tissue removing edge 272 and point 274 distal to removing edge 272 and helical flute 268 is between tissue removing edge 276 and point 278 distal to removing edge 276. Points 274 and 278 recede at from about acute angles with respect to line tangent to the periphery 270 at the points of intersection therewith as described by reference to FIG. 2 above. The curvilinear distances along the periphery 270 of the working portion from tissue removing edge 272 to point 274 may be substantially the same as the curvilinear distance from removing edge 276 to point 278 as illustrated, or the distances may be unequal.

In the illustrated embodiment of FIGS. 13A–C, there are also provided two helical flutes 280 and 282 between tissue removing edges 284 and 272 and between tissue removing edges 286 and 276 which are substantially smaller in volume than flutes 266 ad 268. Again, the curvilinear distance between tissue removing edges 272 and 284 may be substantially the same as the curvilinear distance between tissue removing edges 286 and 276 or the distances may be unequal.

The endodontic instrument 10 illustrated in FIGS. 14A–C, contains three space apart tissue removing edges 290, 292 and 294 defining the working portion periphery 296. Helical flute 298 lies between tissue removing edges 290 and 292, helical flute 300 lies between tissue removing edges 292 and 294 and helical flute 302 lies between tissue removing edges 294 and 290 such that the curvilinear distance along the periphery 296 from removing edge 290 to removing edge 292 is greater than the curvilinear distance from removing edge 292 to removing edge 294 which in turn is greater than the curvilinear distance from removing edge 294 to removing edge 290. In the alternative, the curvilinear distances between removing edges 292 and 294 and removing edges 294 and 290 may be substantially the same. In another alternative, flutes 298, 300 and 302 are all of substantially equal volume.

FIGS. 15A–C represent yet another embodiment of an instrument 10 according to the invention which contains a combination of helical flute designs and one or more recessed helical land portions. In FIGS. 15A–C, there are two helical lands 310 and 312 each having outer land portions 320 and 322 adjacent the periphery 324 defined by tissue removing edge 338 and recessed land portions 314 and 316 which lie at a radial distance $R_1$ from the cross-sectional center 318 of the working portion 14 as illustrated in FIG. 15B. Helical land portions 320 and 322 and helical land 326 all lie adjacent the periphery 324 of the working portion at a distance $R_2$ from the cross-sectional center 318. In this embodiment, helical land 326 does not contain a recessed land portion, however all three lands 310, 312 and 326 may contain recessed land portions.

In the instrument illustrated by FIG. 15B, there are three helical flutes 328, 330 and 332. Helical flute 328 lies between tissue removing edge 334 and point 340 distal to removing edge 334, helical flute 330 lies between tissue removing edge 336 and point 342 distal to removing edge 336 and helical flute 332 lies between tissue removing edge 338 and point 344 distal to removing edge 338. As described above with reference to FIG. 2, points 340 and 342 recede at from about an acute angle with respect to lines tangent to the periphery 324 at the point of intersection thereof. Furthermore, the curvilinear distance from tissue removing edge 338 to point 344 is greater than the curvilinear distance from tissue removing edge 334 to point 340 which in turn is greater than the curvilinear distance between tissue removing edge 336 and point 342. Accordingly, this embodiment combines the recessed land features with the flutes of FIGS. 1–3 and the unequal spacing between adjacent flutes of FIGS. 6A–C.

Figure 16A:
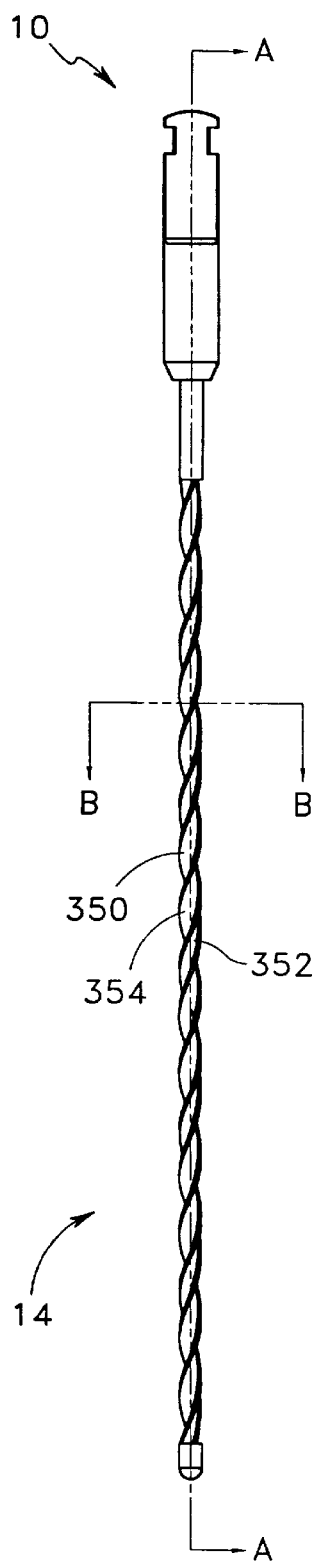
Figure 16B:
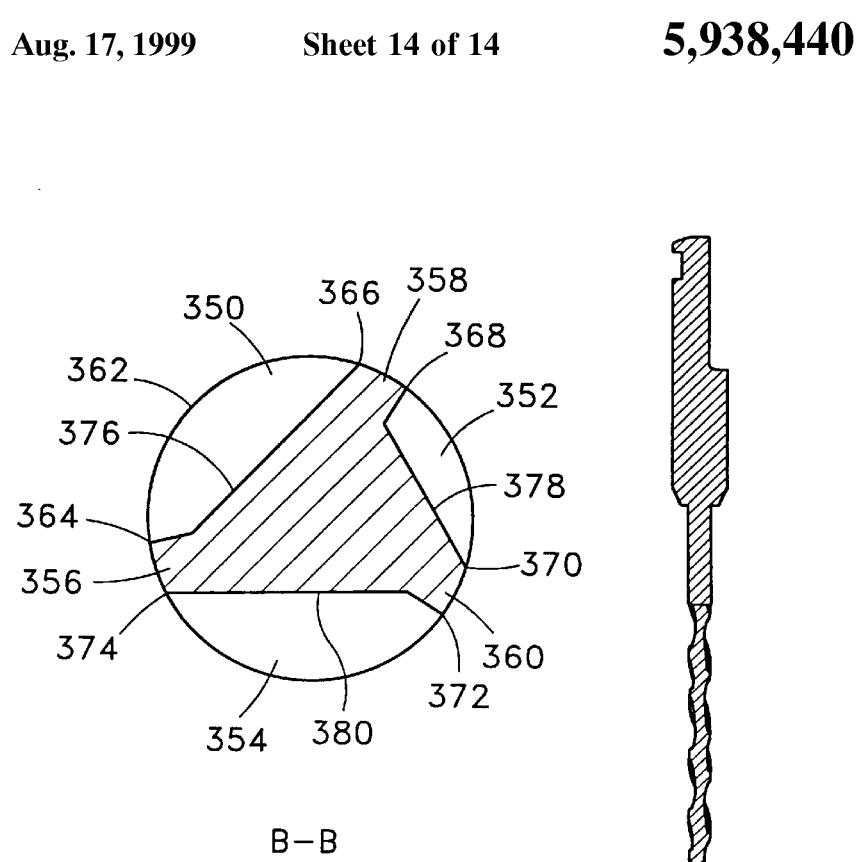
Figure 16C:
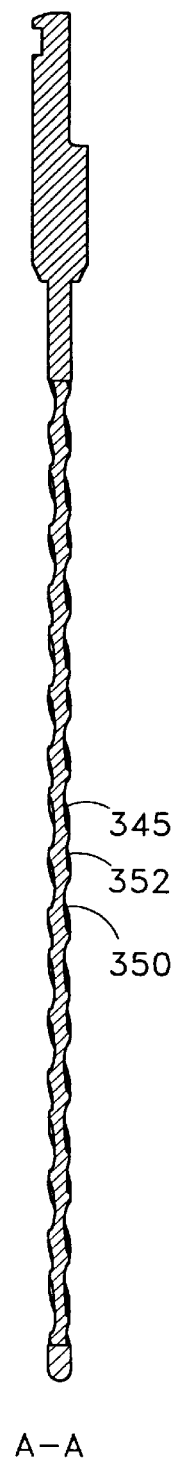

FIGS. 16A–C provide another design of an endodontic instrument 10 of the invention. In this design, there are three helical flutes 350, 352 and 354 in the working portion 14 and three spaced apart helical lands 356, 358 and 360. The curvilinear distance along the periphery 362 of the working portion from tissue removing edge 366 to point 364 distal to removing edge 366 is substantially greater than the curvilinear distance from tissue removing edge 370 to point 368 as shown in FIG. 16B. Likewise, the curvilinear distance along the periphery 362 from tissue removing edge 374 to point 372 is greater than the curvilinear distance from removing edge 370 to point 368 and may be the substantially the same, greater than or less than the curvilinear distance from tissue removing edge 366 to point 364. In this embodiment, the surfaces 376, 378 and 380 of flutes 350, 352 and 354 are angular rather than rounded when viewed in cross-section (FIG. 16B).

As described above with reference to FIG. 2, the points 364, 368 and 372 distal from removal edges 366, 370 and 374 respectively recede at about acute angles with respect to a line tangent to the periphery at the points of intersection therewith. Accordingly, the instrument illustrated by FIGS. 16A–C provide tissue removal efficiencies along the periphery 362 of the working portion which are enhanced by producing a side-cutting effect which more readily maintains the central axis of a curved root canal.

The endodontic instruments of the invention provide reduced resistance during endodontic procedures and/or improved removal of material from the root canal of a tooth because of their design. The endodontic instruments of the invention are also believed to possess improved side cutting capability and an inherent propensity to work into canal areas that are noncircular so as to remove material from nooks previously untouched or insufficiently worked by conventional instruments, as well as to reduce the propensity for the instruments to break during endodontic treatment procedures.

For additional strength, it is preferred that diameter of the web, or uncut core portion of the endodontic instruments of the invention be from about 10 to about 80 percent of the cross-sectional diameter of the working portion. Web diameters greater than about 80 percent may make the instruments too rigid to bend around the curved portions of the root canal while core diameters of less than about 10 percent may not be rigid enough to provide effective cutting or compacting of material in the root canal.

The endodontic instruments of the invention may be used by manipulating the instrument manually in a rotating action, or the instrument may be manipulated by attaching the proximate end (FIG. 1) of the instrument to a motorized device for effecting the removal of material in the root canal.

The rake angles of the tissue removing edges may be positive, negative, or neutral, but are preferably about neutral with respect to the periphery of the working portion. In order to make the instruments having the desired rake angles and configurations, the instruments may be ground from a straight or tapered rod, twisted and/or drawn to a taper with or without grinding.

The endodontic instruments of the invention are preferably made form surgical stainless steel, however, they can also be made from composite materials such as nickel titanium or other "exotic" alloys and the like. The preferred material for the instruments of the invention is nickel titanium or titanium 13-13. Those of ordinary skill will recognize that techniques for making conventional instruments may generally be applied to the manufacture of instruments according to the invention and with various known or later-developed materials. Suitable grinding techniques which may be used are described in metallurgical texts for grinding metals. For example, it is known that certain grinding wheels or bits for making instruments out of one material may not be effective for other or different materials. While a grinding surface made of course grit and rotating at a relatively high speed may be suitable for grinding stainless steel or a hard metal shaft, a nickel-titanium shaft may require a finer grit grinding surface rotating at a relatively slower speed in order to effectively abrade the shaft to form the necessary edges and lands.

The foregoing detailed description is given for understanding of the invention and to illustrate its various features and known advantages, but no unnecessary limitations are to be understood therefrom. Modifications of the various illustrated embodiments and, indeed, the fashioning of other or even improved embodiments, some of which may be obvious to those skilled in the art upon reading the disclosure, may be made without departing from the spirit and scope of the invention as defined by the appended claims.

What is claimed is:

1. An endodontic dental instrument comprising:

a shaft;

an elongate working portion along at least a portion of the length of said shaft; and at least two helical, parallel flutes formed in the working portion of said shaft defining corresponding tissue removing edges substantially at the periphery of said working portion, said tissue removing edges being substantially unequally spaced apart about the periphery of said working portion so as to provide unequal cutting forces along the periphery of said working portion when said instrument is rotated in a root canal;

whereby said instrument more readily maintains the central axis of a curved root canal.

2. The endodontic instrument of claim 1 wherein said flutes have substantially unequal dimensions when viewed in transverse cross-section.

3. The endodontic instrument of claim 1 wherein said flutes are substantially unequally spaced apart about the periphery of said working portion.

4. The endodontic dental instrument of claim 1 further comprising at least one outer land portion at the periphery of said working portion adjacent each said tissue removing edge and at least one recessed land portion.

5. The endodontic dental instrument of claim 4 wherein the recessed land portion has a radius from a cross-sectional center of the instrument to the recessed land portion which is about 4 to 30 percent less than a radius from the cross-sectional center of the instrument to the periphery of the working portion.

6. The endodontic instrument of claim 1 wherein each flute defines at least one point distal from each said tissue removing edge defining a trailing edge of each said flute, each said trailing edge being undercut so as to improve the chip removal capacity of said instrument.

7. An endodontic dental instrument comprising:

a shaft;

an elongate tapered working portion along at least a portion of the length of said shaft;

at least two helical flutes in the working portion of said shaft defining corresponding tissue removing edges at the periphery of said working portion of said shaft, said flutes having a concave shape when viewed in cross-section;

an outer land portion at the periphery of said shaft between adjacent flutes; and a recessed land portion recessed from the periphery of said shaft between adjacent flutes.

8. The endodontic dental instrument of claim 7 wherein the recessed land portion has a substantially constant radius from a cross-sectional center of the instrument to the recessed land portion which is about 4 to 30 percent less than a radius from the cross-sectional center of the instrument to the periphery of the working portion.

9. The endodontic instrument of claim 7 wherein said tissue removing edges are unequally spaced apart about the periphery of said working portion so as to provide unequal cutting forces along the periphery of said working portion when said instrument is rotated in a root canal whereby said instrument more readily maintains the central axis of a curved root canal.

10. The endodontic instrument of claim 7 wherein said flutes have substantially unequal dimensions when viewed in transverse cross-section.

11. The endodontic instrument of claim 7 wherein said flutes are substantially unequally spaced apart about the periphery of said working portion.

12. The endodontic instrument of claim 7 wherein each flute defines at least one point distal from each said tissue removing edge defining a trailing edge of each said flute, each said trailing edge being undercut so as to improve the chip removal capacity of said instrument.

13. An endodontic dental instrument comprising:

a shaft;

an elongate working portion along at least a portion of the length of said shaft; and at least two helical flutes formed in the working portion of said shaft, each said flute defining a tissue removing edge substantially at the periphery of said working portion and a point distal from each said tissue removing edge defining a trailing edge of each said flute, each said trailing edge being undercut to provide increased chip removal capacity when said instrument is rotated in a root canal.

14. The endodontic instrument of claim 13 wherein said tissue removing edges are unequally spaced apart about the periphery of said working portion so as to provide unequal cutting forces along the periphery of said working portion whereby said instrument more readily maintains the central axis of a curved root canal.

15. The endodontic dental instrument of claim 13 further comprising at least one outer land portion at the periphery of said working portion adjacent each said tissue removing edge and at least one recessed land portion.

16. The endodontic dental instrument of claim 15 wherein the recessed land portion has a radius from a cross-sectional center of the instrument to the recessed land portion which is about 4 to 30 percent less than a radius from the cross-sectional center of the instrument to the periphery of the working portion.

* * * * *